US00PP28555P3

(12) United States Plant Patent
Winslow

(10) Patent No.: US PP28,555 P3
(45) Date of Patent: Oct. 24, 2017

(54) ***IPOMOEA* PLANT NAMED 'BALSPOTACK'**

(50) Latin Name: *Ipomoea batatas*
Varietal Denomination: Balspotack

(71) Applicant: Ball Horticultural Company, West Chicago, IL (US)

(72) Inventor: Benjamin K. Winslow, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 79 days.

(21) Appl. No.: 14/998,809

(22) Filed: Feb. 19, 2016

(65) Prior Publication Data

US 2017/0245413 P1 Aug. 24, 2017

(51) Int. Cl.
*A01H 5/08* (2006.01)

(52) U.S. Cl.
USPC ..... Plt./258

(58) Field of Classification Search
USPC ..... Plt./258
See application file for complete search history.

*Primary Examiner* — Anne Grunberg
(74) *Attorney, Agent, or Firm* — Audrey Charles

(57) ABSTRACT

A new and distinct cultivar of an ornamental *Ipomoea* plant named 'Balspotack', characterized by dark purple-colored foliage, and moderately vigorous, compact, mounded to trailing growth habit, is disclosed.

1 Drawing Sheet

Latin name of genus and species of plant claimed: *Ipomoea batatas*.

Variety denomination: 'Balspotack'.

BACKGROUND OF THE INVENTION

The present invention relates to a new and distinct cultivar of *Ipomoea* plant botanically known as *Ipomoea batatas* and hereinafter referred to by the cultivar name 'Balspotack'.

The new cultivar originated in a controlled breeding program in Arroyo Grande, Calif. during November 2012. The objective of the breeding program was the development of ornamental *Ipomoea* cultivars with a well-branched, compact and mounded growth habit with good garden performance under high night temperatures.

The new ornamental *Ipomoea* cultivar is the result of cross-pollination. The female (seed) parent of the new cultivar is ILLUSION Midnight Lace 'NCORNSP-011MNLC', U.S. Plant Pat. No. 21,743, characterized by its purple-colored foliage and compact, semi-upright, densely-mounding growth habit. The male (pollen) parent of the new cultivar is Sweet Caroline Raven 'NCORNSP-015SCPI', U.S. Plant Pat. No. 23,613, characterized by its dark purple-colored foliage and compact, semi-upright, mounding growth habit. The new cultivar was discovered and selected as a single plant within the progeny of the above stated cross-pollination during July 2013 in a controlled environment in Arroyo Grande, Calif.

Asexual reproduction of the new cultivar by terminal stem cuttings since July 2013 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspotack' as a new and distinct cultivar of *Ipomoea* plant:

1. Dark purple-colored foliage; and
2. Moderately vigorous, compact, mounded to trailing growth habit.

Plants of the new cultivar differ from plants of the female parent primarily in having a slightly darker foliage color and a different central lobe shape. Plants of the new cultivar differ from plants of the male parent primarily in having a narrower central lobe and more deeply incised lateral lobes.

Of the many commercially available ornamental *Ipomoea* cultivars, the most similar in comparison to the new cultivar is SolarPower Black 'Balsolablack', U.S. Plant Pat. No. 26,528. However, in comparison, plants of the new cultivar differ from plants of 'Balsolablack' in at least the following characteristics:

1. Plants of the new cultivar are more compact, especially under high night temperatures, than plants of 'Balsolablack';
2. Plants of the new cultivar have foliage that resists discoloration, "burning", especially under high light and high night temperatures, more than plants of 'Balsolablack'; and
3. Plants of the new cultivar have a darker foliage venation color than plants of 'Balsolablack'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balspotack'. The plants were grown in 4.5-inch pots for 5 weeks in a greenhouse in West Chicago, Ill. Plants were pinched at transplant.

DETAILED BOTANICAL DESCRIPTION

Figure 1:
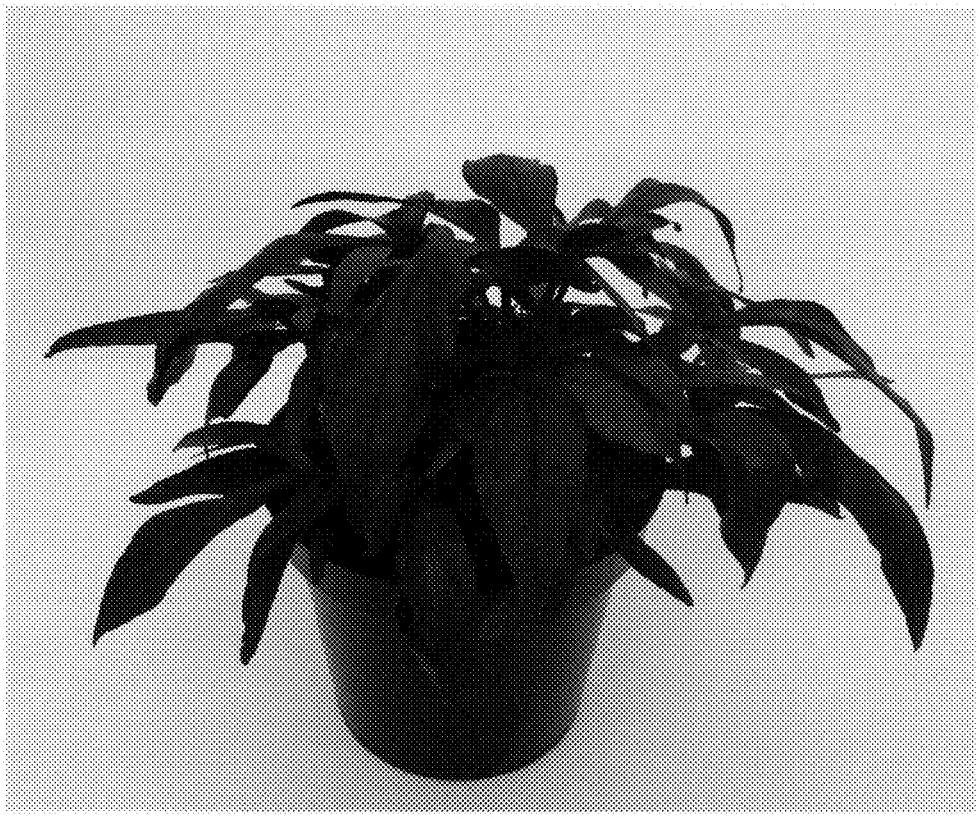
FIG. 1 illustrates a side view of the overall growth and habit of 'Balspotack'.
Figure 2:
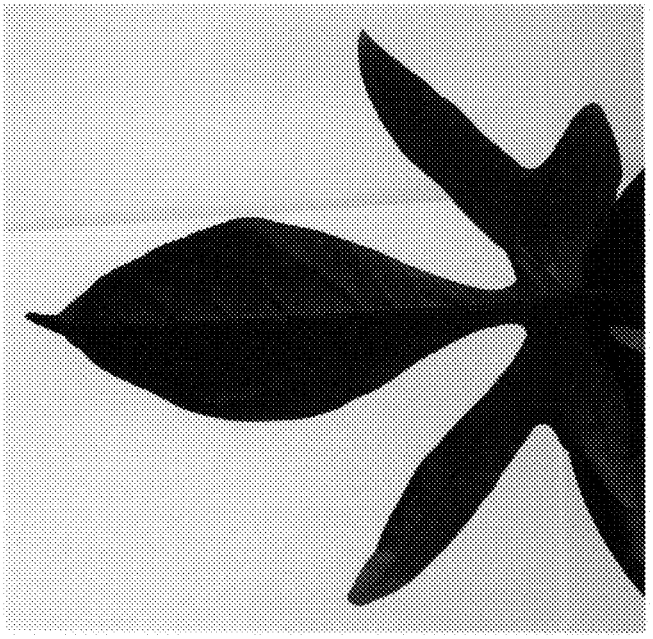
FIG. 2 illustrates a close-up view of an individual leaf of 'Balspotack'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in October 2015 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 5 weeks in a greenhouse utilizing a soilless growth medium. Plants were pinched at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Ipomoea batatas* cultivar Balspotack.

Parentage:

*Female parent.*—ILLUSION Midnight Lace 'NCORNSP-011MNLC', U.S. Plant Pat. No. 21,743.

*Male parent.*—Sweet Caroline Raven 'NCORNSP-015SCPI', U.S. Plant Pat. No. 23,613.

Propagation:

*Type cutting.*—Terminal stem.

*Time to initiate roots.*—Approximately 3 to 4 days.

*Time to produce a rooted cutting.*—Approximately 21 to 28 days.

*Root description.*—Fibrous, medium thickness, white to light brown in color.

*Rooting habit.*—Freely branching.

*Tuber description.*—Not available, tuber formation not observed.

Plant description:

*Commercial crop time.*—Approximately 4 to 5 weeks from a rooted cutting to finish in a 10 cm pot.

*Growth habit and general appearance.*—Moderately vigorous, compact, mounded to trailing growth habit.

*Size.*—Height: Approximately 10.5 cm. Width: Approximately 23.5 cm.

*Branching habit.*—Freely branching, pinching enhances basal branching. Quantity of main lateral branches per plant: Approximately 3, each axil has latent shoots.

*Branch.*—Shape: Round. Strength: Strong, slightly flexible. Length: Approximately 5.0 cm. Diameter: Approximately 3.0 mm. Length of central internode: Approximately 5.0 mm. Texture: Glabrous. Color of young stems: 187B. Color of mature stems: 187A.

Foliage description:

*General description.*—Quantity of leaves per main branch: Approximately 11. Fragrance: None detected. Form: Simple. Arrangement: Alternate, spiral.

*Leaves.*—Shape: Roughly deltoid in overall form, palmately divided with 5 lobes, central lobe elliptic to narrowly elliptic. Margin: Entire. Apex of central lobe: Acuminate. Apex of lateral lobes: Acute. Base: Cordate. Venation pattern: Palmate with arcuate venation in the center lamina. Length of mature leaf: Approximately 10.0 cm. Width of mature leaf: Approximately 8.5 cm. Length of central lobe: Approximately 8.5 cm. Width of central lobe: Approximately 3.5 cm. Texture of upper and lower surfaces: Glabrous. Color of upper surface of young foliage: 144A with an overlay of N186A, venation same color as lamina. Color of lower surface of young foliage: Closest to 146C with midvein of and an overlay of N186C. Color of upper surface of mature foliage: N186A with venation of N186A. Color of lower surface of mature foliage: Closest to N186C with venation of N186D.

*Petiole.*—Length: Approximately 5.0 cm. Diameter: Approximately 3.0 mm. Texture: Glabrous. Color: 187B.

Flowering description: Not available, flower and seed formation not observed. The new ornamental *Ipomoea* cultivar is grown as a foliage plant and is not grown under conditions that are conducive to flower production.

Disease and pest resistance: Resistance to pathogens and pests common to *Ipomoea* has not been observed.

What is claimed is:

1. A new and distinct cultivar of an ornamental *Ipomoea* plant named 'Balspotack', substantially as herein illustrated and described.

* * * * *